United States Patent [19]

Tritsch

[11] 4,063,559

[45] Dec. 20, 1977

[54] DISPOSABLE DIAPER HAVING STRETCHABLE ADHESIVE TAB FASTENERS WITH PARTIBLE PROTECTIVE FILM

[75] Inventor: Ludwig Tritsch, Wilmette, Ill.

[73] Assignee: Johnson & Johnson, New Brunswick, N.J.

[21] Appl. No.: 729,332

[22] Filed: Oct. 4, 1976

[51] Int. Cl.² ............................................. A61F 13/16
[52] U.S. Cl. ..................................... 128/287; 128/284
[58] Field of Search ................... 128/284, 287, 290 R; 24/DIG. 11, 67 AR, 73 VA

[56] References Cited

U.S. PATENT DOCUMENTS

| | | | |
|---|---|---|---|
| 2,510,263 | 6/1950 | Stein | 24/67 AR |
| 3,715,783 | 2/1973 | Parks | 24/67 AR X |
| 3,800,796 | 4/1974 | Jacob | 128/284 |
| 3,853,129 | 12/1974 | Kozak | 128/287 |
| 3,937,221 | 2/1976 | Tritsch | 128/287 |
| 4,010,753 | 3/1977 | Tritsch | 128/284 |

Primary Examiner—Aldrich F. Medbery

[57] ABSTRACT

A disposable diaper is provided with adhesive tab fasteners having a fixed end secured to the diaper and an extendible free end. A pressure-sensitive adhesive coating is provided on one face of the free end and a partible protective cover means is permanently attached to the adhesive coating. The protective cover is substantially coextensive with the adhesive coating when the free end is in a non-extended storage position, but is parted when the free end and adhesive coating are extended to a working position, thereby making portions of the adhesive coating available for use in securing the diaper about an infant. The size and spacing of the exposed adhesive portions on the free end can be controlled to provide adequate adhesive contact for securing the diaper about the infant, while at the same time providing a free end that can be separated from the diaper after affixation for inspecting or repositioning the diaper, and thereafter refastening the diaper.

8 Claims, 9 Drawing Figures

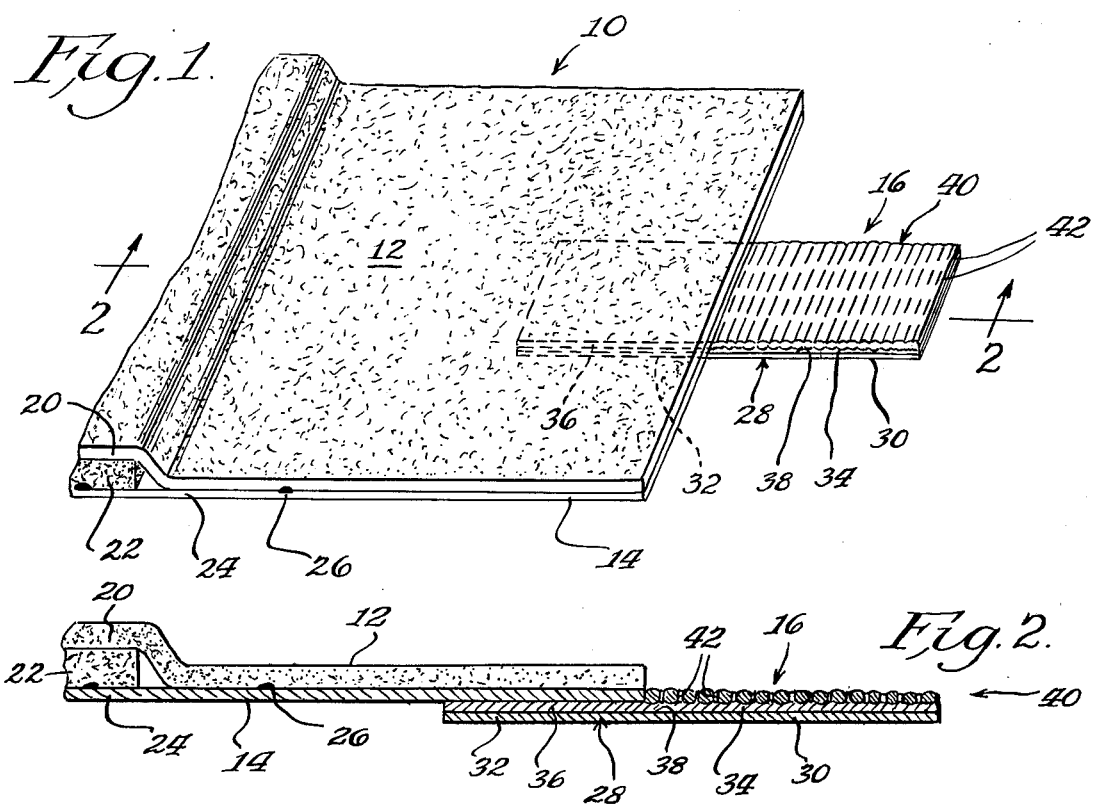
Fig.1.
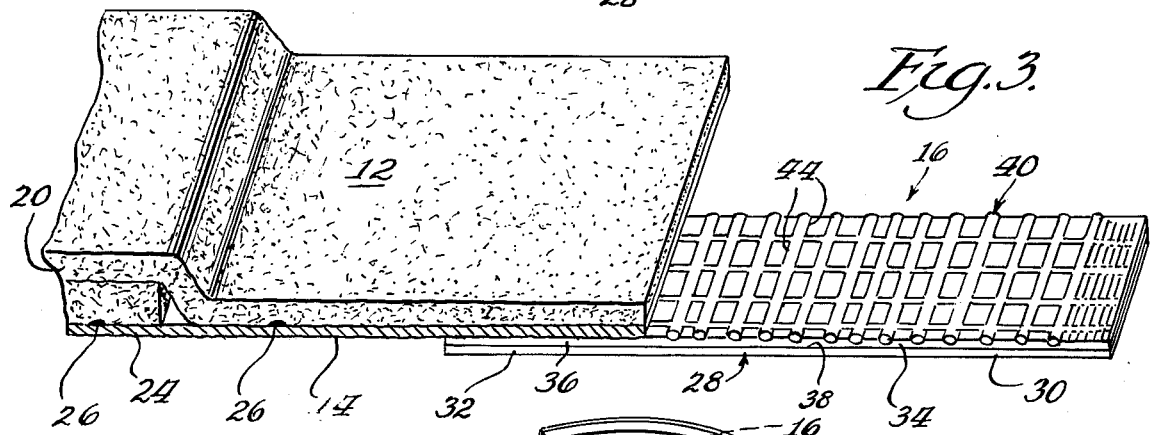
Fig.2.
Fig.3.
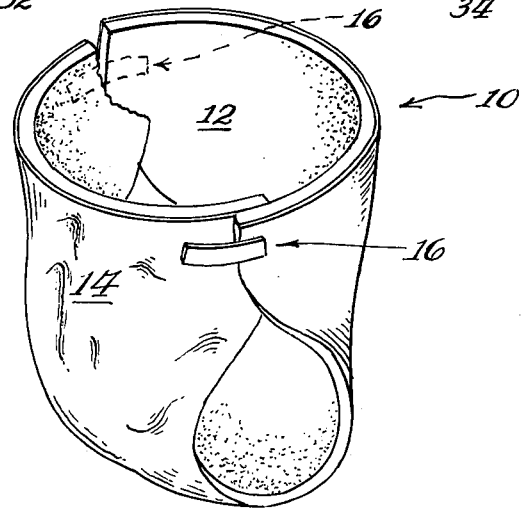
Fig.4.

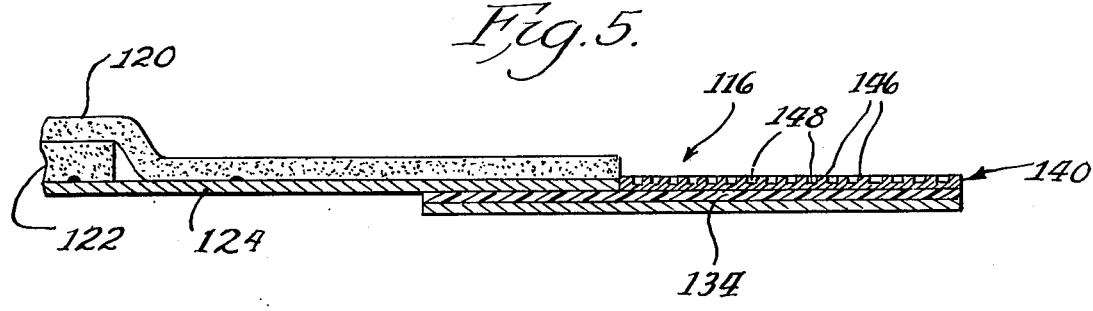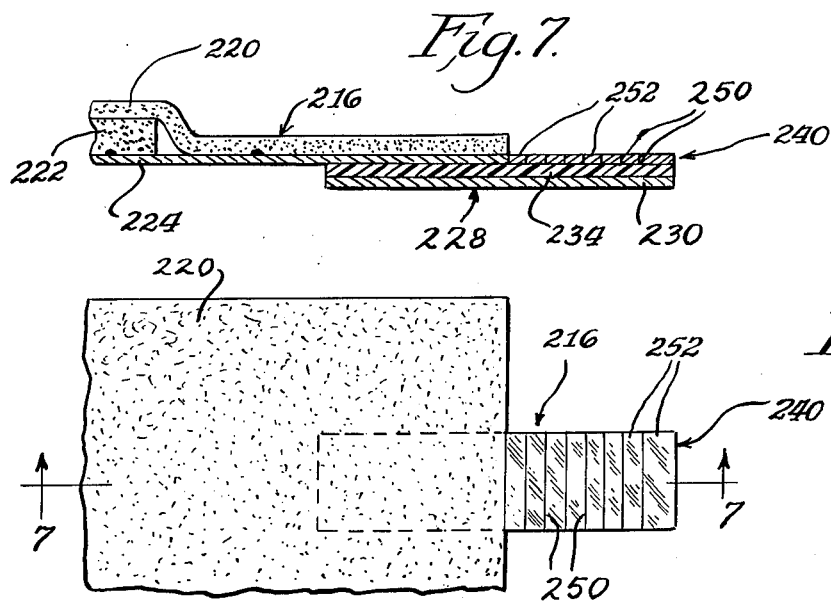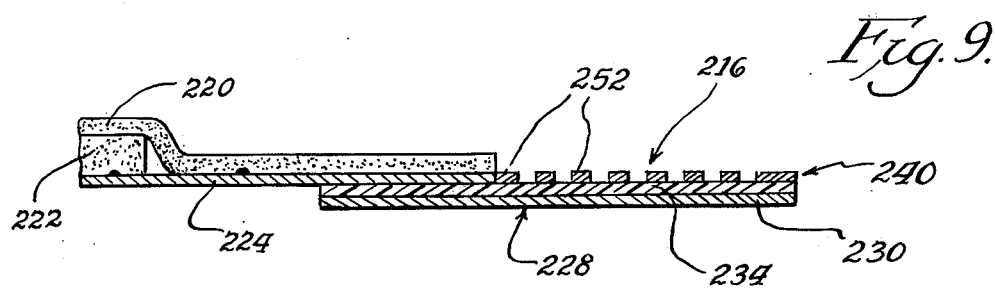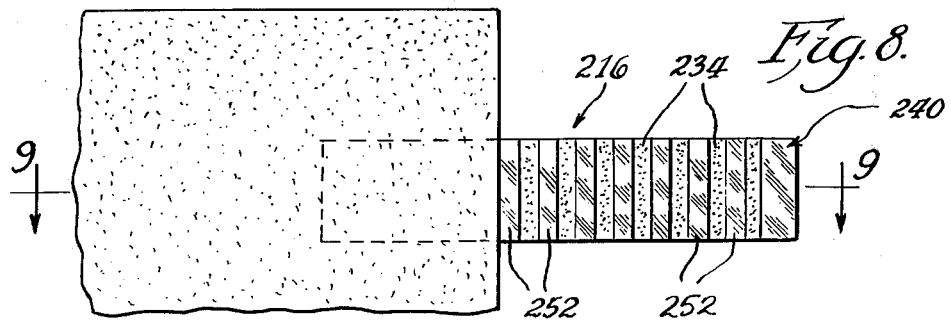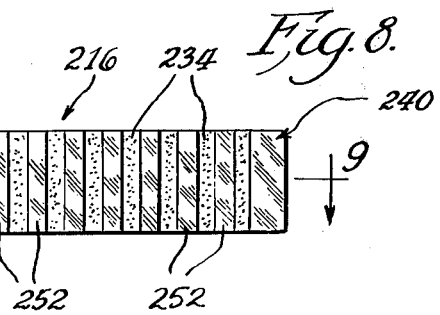

DISPOSABLE DIAPER HAVING STRETCHABLE ADHESIVE TAB FASTENERS WITH PARTIBLE PROTECTIVE FILM

BACKGROUND OF THE INVENTION

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a facing material to be brought into contact with the infant's skin, an absorptive layer of high liquid-holding capacity, and a moisture-impervious backing layer, generally made of a plastic film such as polyethylene film. Typical disposable diaper structures are shown in U.S. Pat. No. 3,612,055 to Mesek et al. and in U.S. Pat. No. Re. 26,151 to Duncan et al.

As may be seen from the above-cited patents, it has been desired to obviate the problems that are inherent in closure systems utilizing extraneous fasteners such as safety pins, snaps and zippers. To this end, adhesive closure systems have presented acceptable solutions.

One of the most convenient adhesive systems that has been developed to date is the system, shown in the above-cited patents, in which adhesive tabs are adhered to the backing sheet extending outwardly from opposite sides of the diaper at one end thereof, with the exposed areas of the adhesive strips having cover strips thereon that are readily separable from the adhesive tabs. Disposable diapers using adhesive closure systems of this general type have the disadvantage of requiring the consumer to dispose of the cover strips when they are separated from the adhesive strips. This is an inconvenience to the consumer who is placing the diaper on an infant.

An illustrative prior art adhesive system having cover strips permanently attached to the diaper is disclosed in U.S. Pat. No. 3,646,937 to Gellert. The Gellert arrangement has the disadvantage of having the release film on the inside of the diaper, where it can possibly come in contact with an infant's tender skin. Additional disadvantages are the complexities and expense which are added to the manufacturing process by requiring each adhesive closure to be manipulated on the front side, around the edge, and onto the back side of the diaper, instead of handling it on one side only. The closure system illustrated in the Gellert patent also makes it somewhat difficult to secure the diaper around an infant, in that it requires the use of two hands to peel back the releasable end of the adhesive tape.

U.S. Pat. No. 3,853,129 to Kozak attempts to solve the foregoing problems by providing adhesive tabs having a fixed end segment attached to the diaper, a middle segment having one face covered with a mesh-like plastic material defining a system of hill portions and valley portions and a releasable working end coated with a pressure-sensitive adhesive and releasably adhered to the hill portions in the middle segment. However, with such an arrangement the available effective adhesive area is limited, the working end of the tab may be subject to displacement transverse to the longitudinal axis, and the tab could be subjected to greater stresses when in use than when the fixed end and the working end of the tab are contiguous.

SUMMARY OF THE INVENTION

According to this invention, a disposable diaper is provided with a pair of adhesive tab fasteners, each comprising a unitary, single, elongated tape segment having a fixed end secured to the diaper along a longitudinal margin thereof, and a free end which has a pressure-sensitive adhesive layer or coating on one face.

A partible protective cover means is substantially coextensive with and permanently adhered to the pressure-sensitive adhesive coating on the free end when the free end is in a non-extended storage position. The free end and the pressure-sensitive adhesive coating are extendible together from the storage position to a working position in which the protective cover is parted, and portions of the pressure-sensitive adhesive coating are exposed through parted portions of the protective cover means for securing the diaper about an infant.

The protective cover can be a web which is provided with discontinuous slits which form discrete apertures when extended; an embossed web which preferentially ruptures in localized regions and forms an open network structure when extended; or a unitary web which is provided with spaced, weakened regions, such as score lines, which rupture when the web is extended. In all cases a portion of the pressure-sensitive adhesive coating is exposed when the protective cover is extended.

It is a feature of the present invention that the adhesive coating is protected by the cover to prevent premature exposure of the adhesive coating when the free end of the tab fastener is in the non-extended storage position, but portions of the adhesive coating are simply and easily exposed when the free end of the tab fastener is extended to part the protective cover. Applicant's arrangement has the further advantage that the protective cover remains as an integral part of the tab and need not be separately disposed. Furthermore, the size and arrangement of the exposed adhesive portions can be controlled to enable the free end of the tab fastener to be detached after an initial securement of the diaper to permit inspection and/or repositioning of the diaper, and can then be used to refasten the diaper about an infant.

BRIEF DESCRIPTION OF THE DRAWINGS

FIG. 1 is a fragmentary perspective view of an open unfolded disposable diaper in accordance with one embodiment of the invention and showing the extendible tab fastener in non-extended, storage position;

FIG. 2 is a cross-sectional view taken along plane 2—2 in FIG. 1;

FIG. 3 is a fragmentary perspective view similar to FIG. 1, and showing the tab fastener in extended, working position;

FIG. 4 is a perspective view of the diaper of FIG. 1 in a configuration assumed by the diaper when placed about an infant;

FIG. 5 is a fragmentary cross-sectional view similar to FIG. 2 and showing another embodiment of the invention in non-extended, storage position;

FIG. 6 is a fragmentary elevational view illustrating an alternate embodiment of the invention with the extendible tab fastener in non-extended, storage position;

FIG. 7 is a cross-sectional view taken along plane 7—7 in FIG. 6;

FIG. 8 is a fragmentary elevational view of the tab fastener of FIG. 6 but showing the tab fastener in extended, working position; and FIG. 9 is a cross-sectional view taken along plane 9—9 in FIG. 8.

DESCRIPTION OF THE PREFERRED EMBODIMENTS

In the following description, two-digit numerals are used to refer to the embodiment illustrated in FIG. 1–4, three-digit numerals of 100 series are used to refer to the embodiment illustrated in FIG. 5, and three-digit numerals of 200 series are used to refer to the embodiment illustrated in FIGS. 6—9. The same last two digits in each numeral designate similar structural elements in the various embodiments.

Disposable diaper 10, illustrated in FIGS. 1–4, is of substantially quadrilateral configuration and presents inside surface 12 for direction toward an infant and outside surface 14 for direction away from the infant. Extendable, unitary adhesive tab fasteners such as tab fastener 16 are attached to diaper 10 for securing diaper 10 about an infant. As described in greater detail below, tab fasteners 16 are movable from a non-extended, storage position illustrated in FIGS. 1 and 2 to an extended, working position as shown in FIG. 3.

Referring to FIGS. 1–3, diaper 10 comprises a moisture-retaining layer made of moisture-pervious facing sheet 20 which defines the diaper inside surface 12 and over-lies absorbent pad 22, and backing sheet 24 which is made of a moisture-impervious material and defines the diaper outside surface 14. Absorbent pad 22 usually is somewhat smaller than backing sheet 24 and is centrally disposed thereon; however, absorbent pad 22 can be made coextensive with backing sheet 24, if desired. Facing sheet 20 is substantially coextensive with backing sheet 24. Both facing sheet 20 and pad 22 can be anchored to backing sheet 24 by means of adhesive beads such as beads 26, glue spots, or in any other convenient manner. For example, if backing sheet 24 is made of a thermoplastic material, facing sheet 20 and pad 22 can be attached thereto by heat bonding.

As illustrated in FIGS. 1–4 adhesive tab fastener 16 comprises an elongated tape segment which includes a backing web 28 having an extendible free working end 30 and a fixed end 32 which is permanently attached to a marginal portion of diaper 10, preferably along outer surface 14.

As shown in FIGS. 2 and 3, free end 30 and fixed end 32 are provided with adhesive coatings 34 and 36 on the inner face 38 of the backing web. Fixed end 32 is attached to backing sheet 24 on diaper outside surface 14 by means of adhesive coating which can be made of a pressure-sensitive adhesive composition, a heat-activated or solvent-activated adhesive composition, or the like. Adhesive coating 34 is coextensive with free end 30 and is pressure-sensitive. Adhesive coatings 34 and 36 preferably comprise a substantially continuous pressure-sensitive layer on inner face 38 of backing web 28 which provides means for securing fixed end 32 to backing sheet 14 and also the pressure-sensitive adhesive layer on inner face 38 of free end 30.

Tab fastener 16 further includes a partible protective cover means 40 which is permanently attached to adhesive coating 34 on free end 30 and substantially coextensive therewith when free end 30 is in a non-extended, storage position, as shown in FIGS. 1 and 2. Free end 30 and pressure-sensitive adhesive coating 34 are extendible from the storage position of FIGS. 1 and 2 to a working position shown in FIG. 3 in which protective cover 40 is parted and portions of the underlying adhesive coating 34 are exposed and thus made available securing the diaper about an infant.

Thus, when tab fastener 16 is in the non-extended storage position, protective cover 40 overlies adhesive coating 34 and minimizes or prevents premature exposure and drying out of adhesive coating 34 as well as premature adhesion to another surface. However, upon extending the free end of tab fastener 16, protective cover 40 is parted and portions of adhesive coating 34 are exposed and are made available for use in securing the diaper about an infant.

Various materials are suitable for use as protective cover 40. In the embodiment illustrated in FIGS. 1–3, protective cover 40 can comprise a thermoplastic material provided with a pattern of spaced slits that open, when extended, to form an open network structure. Thus, the protective cover 40 is extendible and is provided with discontinuous slits 42 (FIGS. 1 and 2) which form discrete apertures 44 (FIG. 3) when protective cover 40 is elongated. Portions of adhesive coating 34 are exposed through the apertures 44 and are available for adhesive securement.

Alternatively, as shown in FIG. 5, protective cover 140 for tab fastener 116 may comprise a rupturable thermoplastic web which is embossed to provide a plurality of main ribs 146 surrounding a plurality of areas of reduced thickness 148. When extended by stretching, the thinnest areas 148 in the web rupture and open up to form an open network structure in which portions of adhesive coating 134 are exposed through the openings in the protective cover. Illustrative webs capable of forming network structures suitable for use with the present invention are disclosed in U.S. Pat. No. 3,914,365 to Kim et al.; U.S. Pat. No. 3,705,070 to Kim; U.S. Pat. No. 3,616,154 to Dow et al.; and U.S. Pat. No. 3,441,638 to Patchell et al.

Another embodiment is illustrated in FIGS. 6–9 wherein the partible protective cover 240 of tab fastener 216 is a rupturable unitary web provided with spaced, weakened regions 250. In the non-extended, storage position illustrated in FIGS. 6 and 7, the substantially continuous portions 252 of protective cover 240 between the weakened regions 250 substantially cover pressure-sensitive adhesive coating 234. When free end 230 of tab fastener 216 is extended, protective cover 240 ruptures along the weakened regions 250, and portions of adhesive coating 234 are exposed between adjacent portions or segments 252. To facilitate rupturing the protective cover 240 upon extension, weakened regions 250 may comprise spaced score lines made up of a plurality of aligned, discontinuous slits, as shown in FIGS. 6 and 7. Preferably, the score lines are situated relatively close to one another. In this embodiment, protective cover 240 ruptures when underlying free end 230 is extended and thus exposes portions of the adhesive coating therebelow.

In all of the embodiments, the adhesion between the free ends such as free end 30 of backing web 28 and the pressure-sensitive adhesive coatings such as coating 34, preferably is greater than the adhesion between protective cover 40 and adhesive coating 34 so that adhesive coating 34 remains anchored to backing web 28 and is exposed through the formed apertures as free end 30 is extended. Also, the apertured protective cover defines a plurality of discrete adhesive regions which enable free end 30 of tab fastener 16 to be detached from and refastened to corner 54 of the diaper (FIG. 4) without damaging tab fastener 16 or the diaper plastic backing sheet 24.

Refastenability is provided by virtue of protective cover 40 which is partially embedded in adhesive coating 34 and projects outwardly from the plane of tab fastener 16. Discrete portions of adhesive coating 34 in the regions defined by apertures 44 are exposed when free end 30 is extended and provide attachment areas which are available for limited but adequate adhesive contact with corner 54 of the diaper when securing the diaper about an infant. The size and arrangement of apertures 44 for adequate adhesion depends on the aggressiveness of the adhesive and the surface properties of the diaper backing, and can be controlled by properly selecting the pattern of slits and/or embossing. Consequently, adhesive contact between the exposed portions of adhesive coating 34 and another surface such as corner 54 of the diaper can be selected so that the free end of tab fastener 16 is separable from corner 54 after initial adhesion thereto so as to permit diaper 10 to be opened for inspection or removed from the infant. The exposed portions of adhesive coating 34 remain available for use in refastening the diaper about an infant.

In a further aspect of the present invention, the tab fastener includes an elastomeric backing web in combination with an extendible protective cover which also exhibits elastomeric properties so that a repositionable tab fastener capable of contraction to a storage position from the extended, working position can be provided. Tab fasteners of this particular type have the additional feature of protecting the pressure-sensitive adhesive coating on the backing web even after the tab fastener has been previously extended and used for diaper securement. For example, backing web 28 in FIG. 3 can be made from an elastomeric web and protective cover 40, overlying adhesive coating 34, can be elastomeric as well, and have an elastic recovery substantially similar to that of backing web 28 at least in the longitudinal direction of the tab fastener. With the foregoing combination of tab fastener elements the adhesive mass of coating 34 is exposed when free working end 30 is stretched and is again covered up when tension in free working end 30 is relaxed. The elasticity of the substantially longitudinal strands in protective cover 40, which interconnect the substantially transverse portions of protective cover 40, assist in the elastic recovery of free working end 30, and, upon contraction thereof, again form a protective covering for adhesive coating 34.

Adhesive tab fasteners suitable for the purposes of the present invention can be extendible or stretchable and can be made from a wide variety of materials, including elastic materials and stretchable materials (i.e., materials having at least some elastic recovery) provided that such materials are sufficiently pliant to be extendible together with protective cover 40. Particularly preferred materials for this purpose are plasticized polyvinyl chloride films, polyolefin films, polyurethane films, vinyl chloride and vinylidene chloride copolymer films, rubber hydrochloride films polyamide films, elastomeric films derived from styrene-butadiene or styrene-isoprene block copolymers, and the like.

The pressure-sensitive adhesive layers such as adhesive coatings 34 and 36 are provided by applying a coating of a pressure-sensitive adhesive composition known in the art to the appropriate surface of backing web 28. The applied adhesive shall have good tack, good cohesive strength, good resistance to moisture and good resistance to aging. In addition, pressure-sensitive adhesive coating 34 should have rheological properties such that the adhesive coating extends together with the underlying free end 30 of backing web 28. Illustrative of such adhesive compositions are mixtures of natural or synthetic rubber, zinc oxide and various resins, also latices of natural or synthetic rubber, or water dispersions of acrylic tacky polymers or copolymers and the like.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,633,348 to Liloia et al.

Facing sheet materials suitable for use in this invention can have fabric weight in the range of about 1 to 5 oz./yd.$^2$ and densities of less than 0.15 g./cc/. generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness and drape characteristics in comparison to prior products incorporating any substantial amount of short fibers.

Facing sheet 20 may also be made of an apertured, non-woven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 20 can be formed of a non-apertured material, such as a nonwoven isotropic web, or the like. In all of the aforementioned facing materials, the material should be relatively hydrophobic so as to retard wicking within the facing layer.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the fastener means. The other end of the diaper then extends downwardly between the infant's legs. Next, the downwardly extending end of the diaper is brought up between the infant's leg's to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by extending the free end of the tabs to expose portions of the adhesive coating. The tabs are then used to secure the diaper in the desired position by simply urging the pressure-sensitive adhesive surfaces in contact with the adjacent outer surface of the diaper. The applied diaper assumes the configuration illustrated in FIG. 4.

The foregoing description and the drawing are illustrative but are not to be taken as limiting. Still other variations and modifications are possible without departing from the spirit and scope of the present invention.

I claim:

1. A disposable diaper having a facing sheet defining a diaper inside surface for direction toward an infant, a moisture-imprevious backing sheet substantially coextensive with said facing sheet and defining a diaper outside surface, an absorbent panel positioned between said facing sheet and said baking sheet, and a pair of stretchable adhesive tab fasteners each comprising:

an elongated tape segment having a fixed end secured to said diaper along a longitudinal margin thereof and an extendible free end;

a pressure-sensitive adhesive layer on one face of said free end;

a means for providing a substantially continuous cover for said free end adhesive when said tab is in its storage position and exposed adhesive when said tab is in its extended working position comprising a partible protective cover means substantially coextensive with and permanently adhered to said pressure-sensitive adhesive layer on said free end when said free end is in a non-extended storage position; said free end and said adhesive layer being extendible together from the storage position to a working position in which said protective cover means is parted and a portion of said pressure-sensitive adhesive layer is exposed for securing said diaper about an infant.

2. The disposable diaper as defned in claim 1 wherein said partible protective cover means is extendible and is provided with discontinuous slits which form discrete apertures when stretched, and wherein a portion of said pressure-sensitive adhesive layer is exposed through said apertures.

3. The disposable diaper as defined in claim 1 wherein said partible protective cover means is an embossed, rupturable thermoplastic web which forms an open network structure when stretched.

4. The disposable diaper as defined in claim 1 wherein said partible protective cover means is a unitary web provided with spaced, weakened regions which rupture when the web is stretched.

5. The disposable diaper as defined in claim 1 wherein said partible protective cover means is a rupturable unitary web provided with spaced score lines which part when the web is stretched.

6. The disposable diaper as defined in claim 1 wherein an adhesive layer is provided on one face of said fixed end by means of which said fixed end is secured to said diaper, and said adhesive layers on said fixed end and said free end comprise a substantially continuous pressure-sensitive adhesive layer on one face of said elongated tape segment.

7. The disposable diaper as defined in claim 1 wherein said parted protective cover means defines a plurality of discrete portions of exposed adhesive in said adhesive layer available for adhesive contact with said diaper and sufficient to secure said diaper about an infant but permitting said free end to be separated from said diaper after securement thereto, thereby making said exposed portion of said adhesive layer on said free end available for use in refastening said diaper about an infant.

8. The disposable diaper as defined in claim 1 wherein said extendible free end and said partible protective cover means are elastomeric.

* * * * *